United States Patent
Funahashi

(10) Patent No.: US 7,082,215 B1
(45) Date of Patent: Jul. 25, 2006

(54) IMAGE PROCESSING METHOD AND APPARATUS

(75) Inventor: Takeshi Funahashi, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/568,047

(22) Filed: May 10, 2000

(30) Foreign Application Priority Data

May 10, 1999 (JP) ................................. 11-127962

(51) Int. Cl.
*G06K 9/00* (2006.01)
(52) U.S. Cl. ..................................... 382/128; 348/231.2
(58) Field of Classification Search ................ 382/128, 382/224
See application file for complete search history.

(56) References Cited

U.S. PATENT DOCUMENTS

| 5,019,975 A | * | 5/1991 | Mukai ............................ 707/7 |
| 5,173,787 A | * | 12/1992 | Mitani .......................... 382/232 |
| 5,270,530 A | * | 12/1993 | Godlewski et al. ...... 250/208.1 |
| 5,276,805 A | * | 1/1994 | Hamaguchi ................. 345/537 |
| 5,779,634 A | * | 7/1998 | Ema et al. ................... 600/407 |
| 6,160,579 A | * | 12/2000 | Shiraiwa et al. ......... 348/224.1 |

OTHER PUBLICATIONS

"Windows NT 4.0 MCSE Study Guide" by Carter, IDG Books Worldwide, Inc, 1997, pp. 466-477.*

* cited by examiner

Primary Examiner—Samir Ahmed
Assistant Examiner—Charles Kim
(74) Attorney, Agent, or Firm—Sughrue Mion, PLLC

(57) ABSTRACT

In an image processing method, predetermined processing is performed with respect to a plurality of image signals, each of which is appended with grouping information representing that image signals appended with identical grouping information represent images associated with one another. In cases where the predetermined processing is performed with respect to a specific image signal, the predetermined processing is also performed with respect to all of image signals, which are appended with the same grouping information as the grouping information appended to the specific image signal. The predetermined processing may be image processing performed on the image signal or a processing for altering subsidiary information appended to the image signal.

10 Claims, 5 Drawing Sheets

IMAGE PROCESSING METHOD AND APPARATUS

BACKGROUND OF THE INVENTION

1. Field of the Invention

This invention relates to an image processing method and apparatus, wherein processing for altering image processing and/or subsidiary information appended to an image signal is performed with respect to a plurality of image signals, which represent images associated with one another. This invention also relates to a recording medium, on which a program for causing a computer to execute the image processing method has been recorded and from which the computer is capable of reading the program.

2. Description of the Prior Art

Images of objects, such as patients, have heretofore been recorded with image input modalities, such as computed radiography (CR) apparatuses, computed tomography (CT) scanners, and magnetic resonance imaging (MRI) apparatuses. An image signal representing the thus recorded image is utilized for reproducing a visible image and displaying it on a monitor. A medical doctor can make a diagnosis of an illness by referring to the visible image displayed on the monitor. In such cases, a plurality of images associated with one another, e.g. the images of a single patient or the images having been recorded in a single examination, may be displayed together on the monitor, and the medical doctor can make a diagnosis of an illness by seeing the displayed images.

When an image signal is generated by an image input modality, grouping information, such as the name of the patient, the examination number, the series number within an identical examination number, the date of examination, and/or identification (ID) information, is appended to the image signal. Therefore, by the utilization of the ID information appended to each of image signals, a plurality of image signals can be associated with one another and grouped in accordance with the name of the patient, the examination number, the series number within an identical examination number, and/or the date of examination.

In cases where a visible image is to be reproduced from an image signal and displayed on a monitor, image processing, such as gradation processing, processing in the frequency domain, or color transform processing, is often performed on the image signal. In such cases, the image signal to be subjected to the image processing is selected on the monitor, and the image processing is performed on the selected image signal. However, in cases where the same image processing as that having been performed on a certain image signal is to be performed also on all of the other image signals of the group, to which the certain image signal belongs, it has heretofore been necessary that all of the other image signals of the group, to which the certain image signal belongs, are selected successively on the monitor, and the image processing is performed on each of the successively selected image signals. With the conventional technique, considerable time and labor are required to perform the processing in this manner.

Also, when the grouping information is inputted in an image input modality, it often occurs that, with respect to an image signal belonging to a certain group, grouping information belonging to a different group is given by mistake. Further, it often occurs that an incorrect file name is given by mistake to an image signal. In such cases, the image signal, which has been assigned with the incorrect grouping information or the incorrect file name, must be found out, and processing for altering the grouping information or the file name must be performed on the image signal. However, if the grouping information or the file name must be altered in this manner, considerable time and labor will be required to find out, the image signal.

SUMMARY OF THE INVENTION

The primary object of the present invention is to provide an image processing method, wherein processing is capable of being performed easily with respect to image signals representing images associated with one another.

Another object of the present invention is to provide an apparatus for carrying out the image processing method.

A further object of the present invention is to provide a recording medium, on which a program for causing a computer to execute the image processing method has been recorded and from which the computer is capable of reading the program.

The present invention provides a first image processing method, wherein predetermined processing is performed with respect to a plurality of image signals, each of which is appended with grouping information, wherein the image signals appended with identical grouping information represent images associated with one another, the method comprising the steps of:

in cases where the predetermined processing is performed with respect to a specific image signal, performing the predetermined processing with respect to all of image signals, which are appended with the same grouping information as the grouping information appended to the specific image signal.

The term "grouping information" as used herein means the information, with which the image signals are capable of being classified into a group for each patient name, each examination number, or the like, such as the name of the patient, the examination number, the series number within an identical examination number, the date of examination, and/or an ID number appended to the image signal, which are appended to the image signal when, for example, the image signal is generated.

In the first image processing method in accordance with the present invention, the predetermined processing may be image processing performed on the image signal. Alternatively, the predetermined processing may be a processing for altering subsidiary information appended to the image signal.

The term "subsidiary information appended to an image signal" as used herein means the information, such as the grouping information described above, the file name of the image signal, and the image processing information, which gives specifics about image processing and is appended to the image signal.

The present invention also provides a second image processing method, comprising the steps of:

i) selecting a specific image signal from a plurality of image signals, each of which is appended with grouping information, wherein the image signals appended with identical grouping information represent images associated with one another, ii) selecting at least one predetermined piece of information from the pieces of information constituting the grouping information appended to the specific image signal, iii) selecting all of image signals, which are appended with the same piece of information as the predetermined piece of information having been selected from the pieces of information constituting the grouping information appended to the specific image signal, from the plurality of the image signals, and iv) performing processing on all of the image signals having thus been selected, the processing being performed for reflecting subsidiary information, which is appended to the specific image signal, on the image signals.

In the second image processing method in accordance with the present invention, as the predetermined piece of information, only one piece of information, which is among the pieces of information constituting the grouping information, may be selected. Alternatively, a plurality of pieces of information, which are among the pieces of information constituting the grouping information, may be selected as the predetermined piece of information.

The present invention further provides a first image processing apparatus, comprising processing means for performing predetermined processing with respect to a plurality of image signals, each of which is appended with grouping information, wherein the image signals appended with identical grouping information represent images associated with one another, wherein the processing means operates such that, in cases where the processing means performs the predetermined processing with respect to a specific image signal, the processing means also performs the predetermined processing with respect to all of image signals, which are appended with the same grouping information as the grouping information appended to the specific image signal.

In the first image processing apparatus in accordance with the present invention, the predetermined processing may be image processing performed on the image signal. Alternatively, the predetermined processing may be a processing for altering subsidiary information appended to the image signal.

The present invention still further provides a second image processing apparatus, comprising:

i) means for selecting a specific image signal from a plurality of image signals, each of which is appended with grouping information representing that image signals appended with identical grouping information represent images associated with one another, ii) means for selecting at least one predetermined piece of information from the pieces of information constituting the grouping information appended to the specific image signal, iii) means for selecting all of image signals, which are appended with the same piece of information as the predetermined piece of information having been selected from the pieces of information constituting the grouping information appended to the specific image signal, from the plurality of the image signals, and iv) means for performing processing on all of the image signals having thus been selected, the processing being performed for reflecting subsidiary information, which is appended to the specific image signal, on the image signals.

The present invention also provides a recording medium, on which a program for causing a computer to execute the first image processing method in accordance with the present invention has been recorded and from which the computer is capable of reading the program.

The present invention further provides a recording medium, on which a program for causing a computer to execute the second image processing method in accordance with the present invention has been recorded and from which the computer is capable of reading the program.

With the first image processing method and apparatus in accordance with the present invention, when the predetermined processing is performed with respect to the specific image signal, the same predetermined processing is also performed with respect to all of image signals, which are appended with the same grouping information as the grouping information appended to the specific image signal. Therefore, in cases where the same processing is to be performed with respect to all of the image signals, which are appended with the same grouping information, it is unnecessary that the image signals are selected one after another and the processing is performed successively with respect to the selected image signals. Accordingly, the predetermined processing can be performed easily and efficiently with respect to the image signals.

With the second image processing method and apparatus in accordance with the present invention, the specific image signal is selected from the plurality of the image signals. At least one predetermined piece of information is selected from the pieces of information constituting the grouping information appended to the specific image signal. Also, all of image signals, which are appended with the same piece of information as the predetermined piece of information having been selected from the pieces of information constituting the grouping information appended to the specific image signal, are selected from the plurality of the image signals. Thereafter, the subsidiary information, which is appended to the specific image signal, is reflected upon all of the image signals having thus been selected.

When the subsidiary information, such as the grouping information, the name of file, and/or the image processing information, is appended to image signals, it may occur that different subsidiary information is appended by mistake to certain image signals, which are among the image signals belonging to the same group. In such cases, it is necessary for operations to be performed for finding out the image signals appended with the incorrect subsidiary information and correcting the subsidiary information appended to the image signals. However, it may occur that incorrect subsidiary information is inputted at the time of the correction or necessary correction is not made perfectly. However, as for the grouping information appended to image signals, if an incorrect piece of information is given by mistake among the pieces of information constituting the grouping information, it will not occur that all of the other pieces of information constituting the grouping information are incorrect. Therefore, with the second image processing method and apparatus in accordance with the present invention, an image signal appended with correct grouping information is selected as the specific image signal, and the subsidiary information appended to the specific image signal is reflected upon all of the image signals, which are appended with the same piece of information as the predetermined piece of information having been selected from the pieces of information constituting the grouping information appended to the specific image signal. Accordingly, error in correction or imperfect correction do not occur. Also, consistency of the subsidiary information can be obtained easily with respect to the image signals appended with the same grouping information.

DESCRIPTION OF THE PREFERRED EMBODIMENTS

The present invention will hereinbelow be described in further detail with reference to the accompanying drawings.

Figure 1:
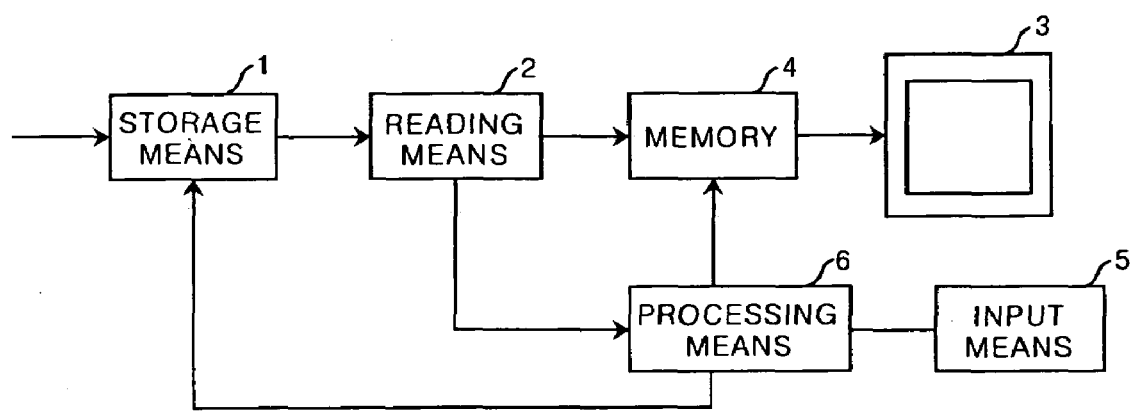
FIG. 1 is a schematic block diagram showing a first embodiment of the image processing apparatus in accordance with the present invention.

FIG. 1 is a schematic block diagram showing a first embodiment of the image processing apparatus in accordance with the present invention. As illustrated in FIG. 1, the first embodiment of the image processing apparatus in accordance with the present invention comprises storage means 1 for storing image signals, and reading means 2 for reading image signals from the storage means 1. The image processing apparatus also comprises a monitor 3 for reproducing visible images from several image signals having been read by the reading means 2 from the storage means 1 and displaying the reproduced images, and a memory 4 for temporarily storing the image signals other than the several image signals, from which the visible images can be reproduced simultaneously on the monitor 3. The image processing apparatus further comprises input means 5, which may be constituted of a keyboard and a mouse device and from which various pieces of information are inputted into the image processing apparatus. The image processing apparatus still further comprises processing means 6 for performing image processing on image signals.

Figure 2:
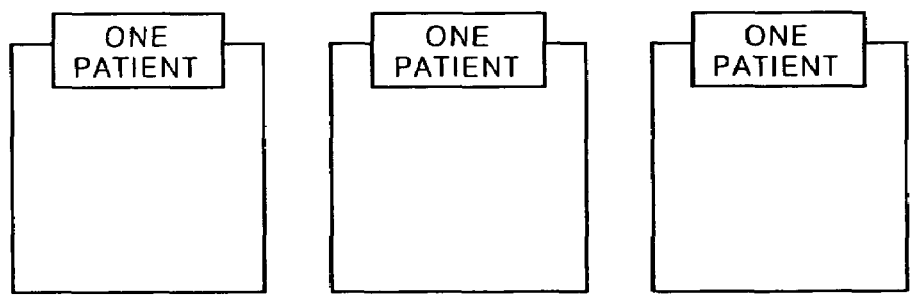
FIG. 2 is an explanatory view showing image signals grouped for each patient.
Figure 3:
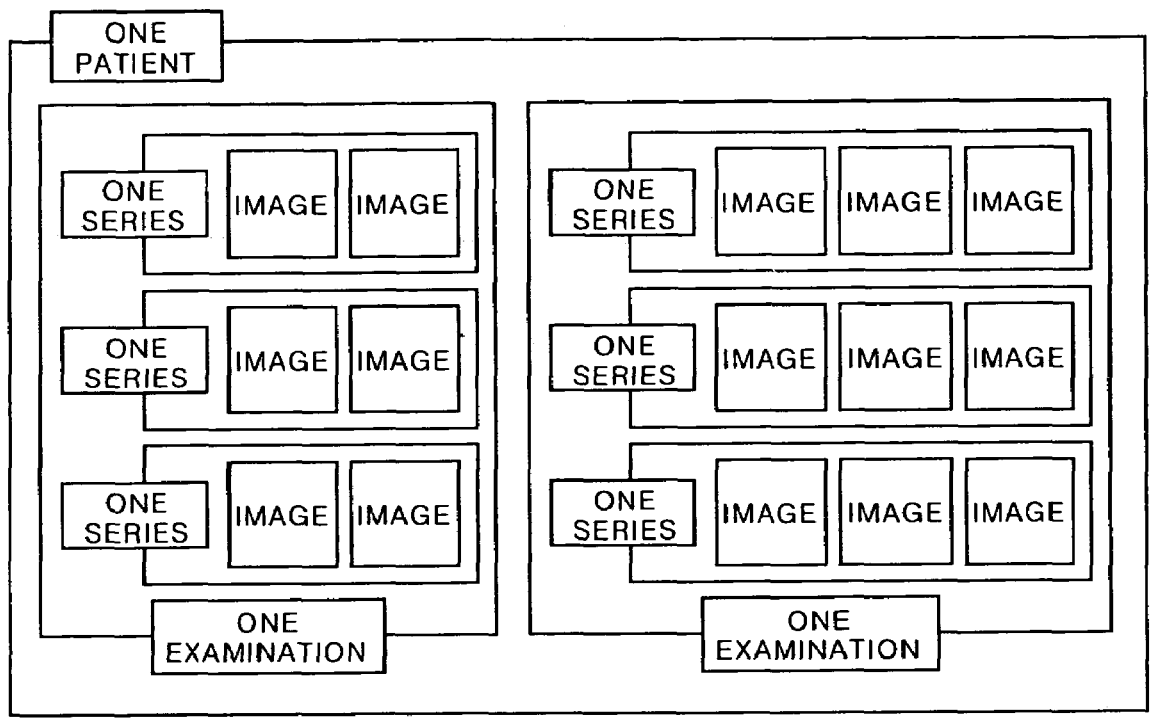
FIG. 3 is an explanatory view showing image signals grouped for each patient, each examination, and each series in each examination.
Figure 4:
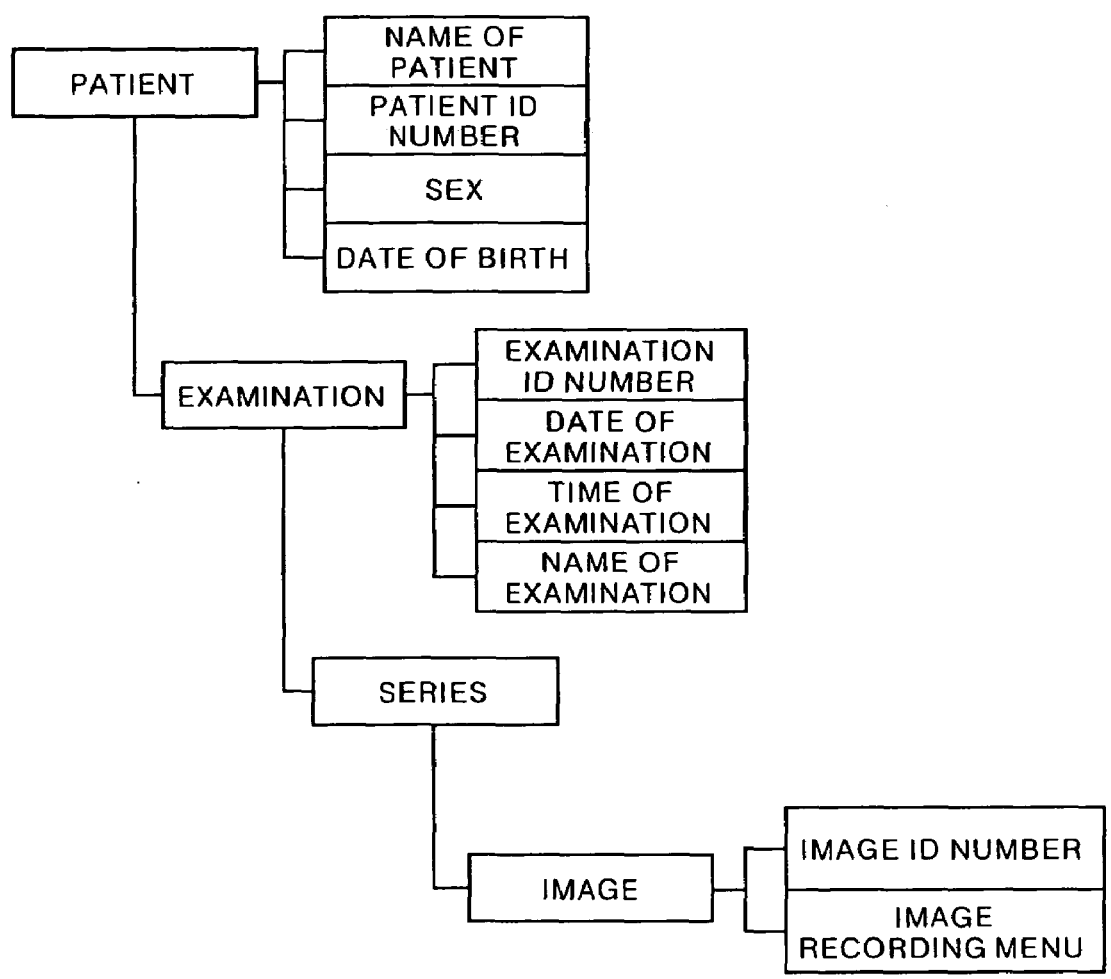
FIG. 4 is an explanatory view showing a different example of how grouping information is appended.

The image signals are generated by image input modalities (not shown), such as CR apparatuses, CT scanners, and MRI apparatuses. When the image signals are generated, information representing the name of the patient, the examination number, and the series number within the identical examination number is appended as grouping information to each of the image signals. Therefore, as illustrated in FIG. 2, image signals can be classified into a group for each patient. Also, as illustrated in FIG. 3, the image signals representing the images of each patient can be classified into a group for each examination. Further, the image signals belonging to the group for each examination can be classified into a group for each series in one examination. Alternatively, the grouping information may be given in more detail for each patient, each examination, each series, and each image. For example, as illustrated in FIG. 4, as the grouping information for a patient, the name of the patient, the patient ID number, the sex of the patient, and the date of birth of the patient may be appended. Also, as the grouping information for an examination, the examination ID number, the date of examination, the time of the examination, and the name of examination may be appended. Further, as the grouping information for an image, the image ID number and the image recording menu employed in the operation for recording the image may be appended.

Figure 5:
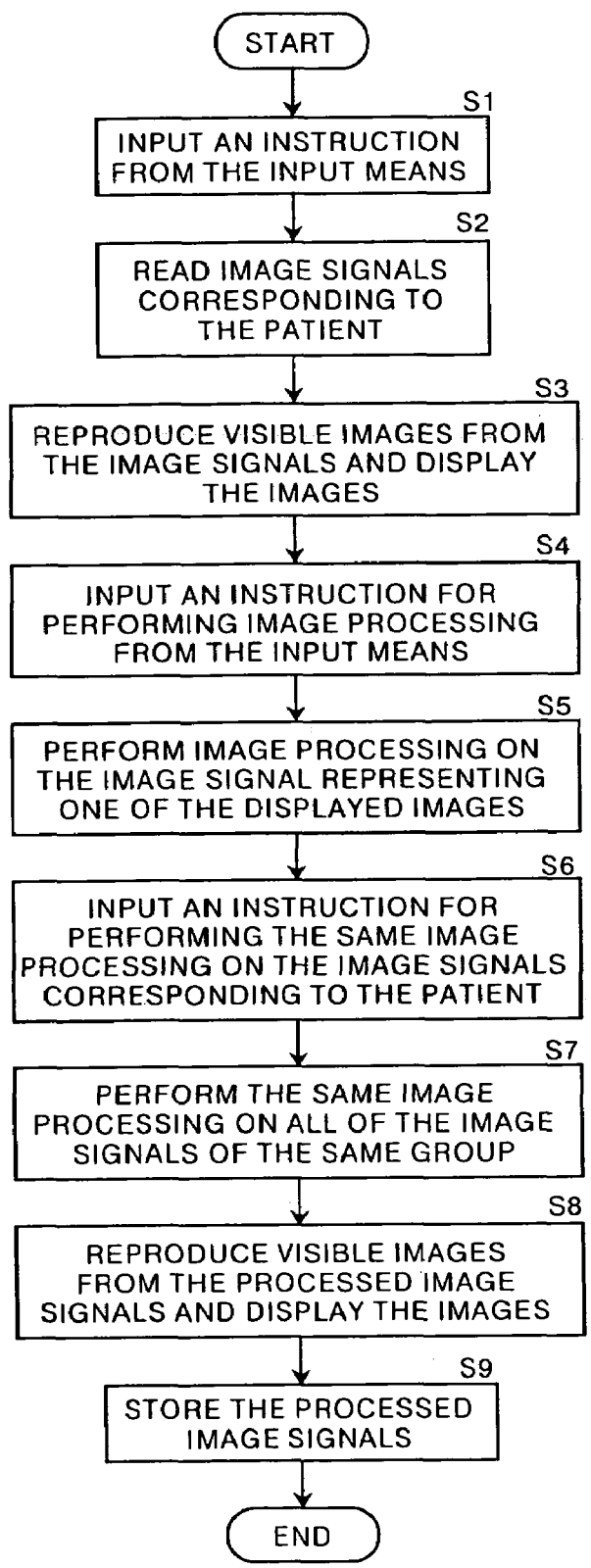
FIG. 5 is a flow chart showing how the first embodiment of FIG. 1 operates.

How the first embodiment of the image processing apparatus in accordance with the present invention operates will be described hereinbelow with reference to FIG. 5. FIG. 5 is a flow chart showing how the first embodiment of FIG. 1 operates. Firstly, in a step S1, an instruction is inputted from the input means 5 in order to reproduce visible images on the monitor 3 from image signals, which represent the images of a certain patient and which are among the image signals stored in the storage means 1. In a step S2, the reading means 2 receives the instruction and reads all of the image signals, which are appended with the grouping information containing the name of the patient, from the storage means 1. In a step S3, the thus read image signals are fed through the memory 4 into the monitor 3, and the images represented by the image signals are reproduced and displayed on the monitor 3. The monitor 3 can display only a predetermined number of (e.g., five) images at one time. Therefore, the image signals other than the predetermined number of image signals, from which the visible images can be reproduced simultaneously on the monitor 3, are kept temporarily stored in the memory 4.

In a step S4, in cases where image processing, such as gradation processing, processing in the frequency domain, or color transform processing, is to be performed on one of the images displayed on the monitor 3, an instruction for performing the image processing is inputted from the input means 5. In a step S5, the image processing is performed on the image signal representing one of the images which are displayed on the monitor 3. At this time, in a step S6, an instruction for performing the same image processing on the image signals, which represent the images of the patient, is inputted from the input means 5. In a step S7, the same image processing is performed by the processing means 6 on all of the image signals, which are appended with the grouping information containing the name of the patient, i.e. all of the image signals having been read by the reading means 2 from the storage means 1, and processed image signals are thereby obtained. In cases where an instruction for performing the image processing on the image signals, which have been obtained in a certain examination of the patient, is inputted from the input means 5, the image signals, which are appended with the grouping information containing the examination number corresponding to the certain examination, are extracted from the image signals having been read by the reading means 2 from the storage means 1, and the image processing is performed on the thus extracted image signals, the processed image signals being thereby obtained. In cases where an instruction for performing the image processing on the image signals, which have been obtained in a certain series in a certain examination of the patient, is inputted from the input means 5, the image signals, which are appended with the grouping information containing the series number corresponding to the certain series in the certain examination, are extracted from the image signals having been read by the reading means 2 from the storage means 1, and the image processing is performed on the thus extracted image signals, the processed image signals being thereby obtained.

In a step S8, the visible images are reproduced from the thus obtained processed image signals and displayed on the monitor 3. In a step S9, after confirmation is made by the operator, the processed image signals are fed back to the storage means 1 and stored in the storage means 1.

As described above, in the first embodiment, when the image processing is performed on the image signal representing one of the images displayed on the monitor 3, the same image processing is also performed on the image signals corresponding to the same patient, the same examination number, and/or the same series number as that with respect to the image signals representing the images displayed on the monitor 3. Therefore, it is unnecessary to perform the image processing successively on the respective image signals. Accordingly, the image processing can be performed easily and efficiently on the image signals appended with the same grouping information.

In the first embodiment described above, the image processing, which has been performed on a certain image signal among the image signals representing the images displayed on the monitor 3, is also performed on the image signals, which are appended with the same grouping information as the grouping information appended to the certain image signal. However, in such cases, the images need not necessarily be displayed on the monitor 3. Alternatively, an instruction for performing the same image processing on the image signals, which are appended with the same grouping information, may be inputted from the input means 5, and the image signals appended with the specified grouping information may then be read by the reading means 2 from the storage means 1. Thereafter, the same image processing may be performed on the thus read image signals.

When the subsidiary information, such as the grouping information, the name of file, and/or the image processing information, is appended to image signals in the image input modality, it may occur that different subsidiary information is appended by mistake to certain image signals, which are among the image signals belonging to the same group. However, as for the grouping information appended to image signals, if an incorrect piece of information is given by mistake among the pieces of information constituting the grouping information, it will not occur that all of the other pieces of information constituting the grouping information are incorrect. Therefore, in the first embodiment described above, when the subsidiary information is to be corrected with respect to a certain image signal having been appended with the incorrect subsidiary information, an instruction for correcting the subsidiary information with respect to all of the image signals, which are appended with the same grouping information as the grouping information appended to the certain image signal, may be inputted from the input means 5. In this manner, the processing for correcting the subsidiary information can be performed efficiently.

A second embodiment of the image processing apparatus in accordance with the present invention will be described hereinbelow. Basically, the second embodiment of the image processing apparatus in accordance with the present invention has the same constitution as the first embodiment of the image processing apparatus in accordance with the present invention. In the second embodiment, a specific image signal is selected with the input means 5. In the processing means 6, all of image signals, which are appended with the same piece of information as a predetermined piece of information having been selected from the pieces of information constituting the grouping information appended to the specific image signal, are selected. Also, in the processing means 6, processing for reflecting the subsidiary information, which is appended to the specific image signal, upon an image signal is performed on all of the image signals having thus been selected.

In the second embodiment, the input means 5 acts as the means for selecting a specific image signal from a plurality of image signals, each of which is appended with grouping information, wherein the image signals appended with identical grouping information represent images associated with one another, the means for selecting at least one predetermined piece of information from the pieces of information constituting the grouping information appended to the specific image signal, and the means for selecting all of image signals, which are appended with the same piece of information as the predetermined piece of information having been selected from the pieces of information constituting the grouping information appended to the specific image signal, from the plurality of the image signals.

Figure 6:
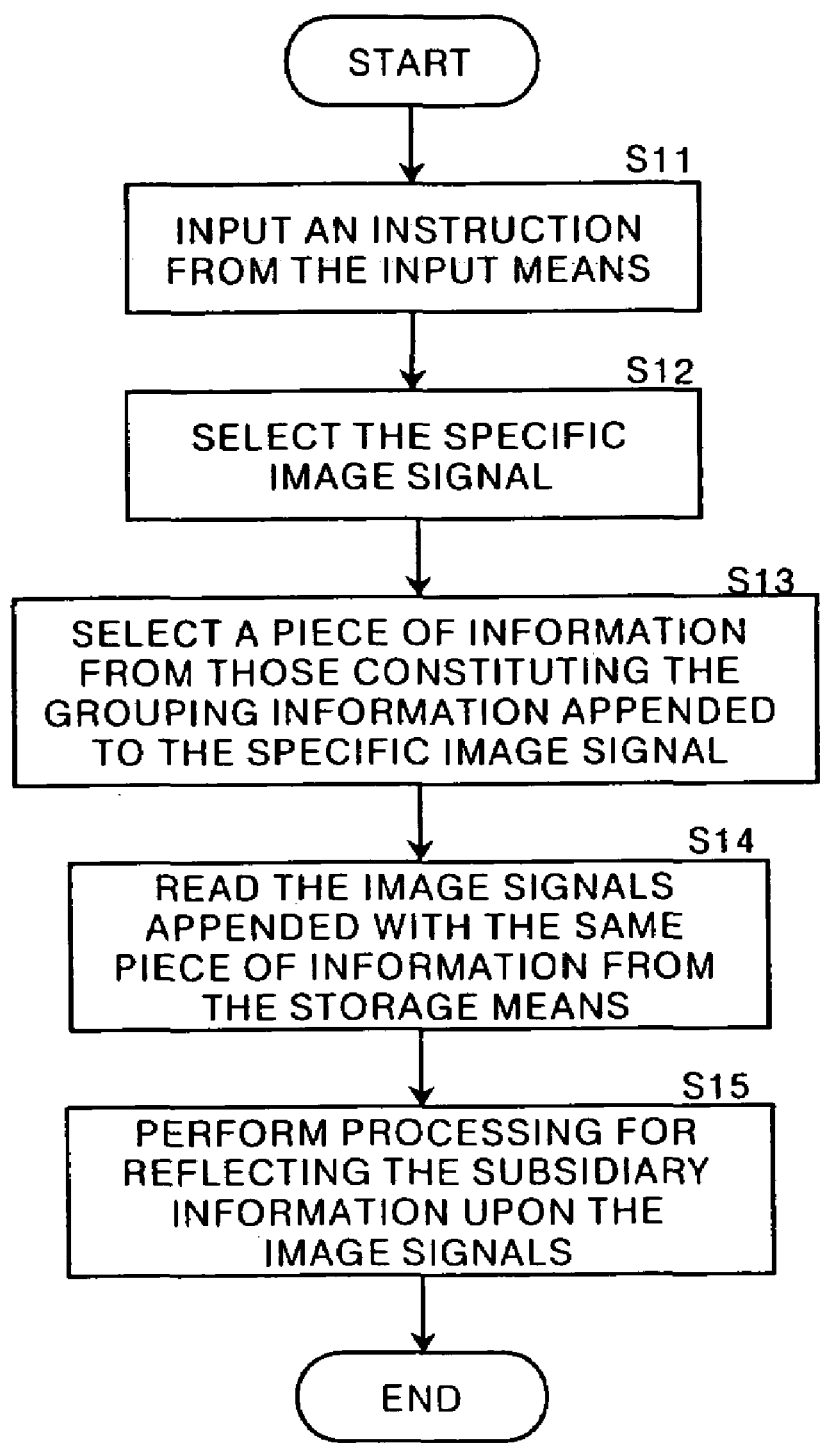
FIG. 6 is a flow chart showing how a second embodiment of the image processing apparatus in accordance with the present invention operates.

How the second embodiment operates will be described hereinbelow with reference to FIG. 6. FIG. 6 is a flow chart showing how the second embodiment of the image processing apparatus in accordance with the present invention operates. Firstly, in a step S11, an instruction is inputted from the input means 5 in order to select a specific image signal from the image signals stored in the storage means 1. In a step S12, the reading means 2 receives the instruction and selects the specific image signal. In a step S13, an instruction is inputted from the input means 5 in order to select a predetermined piece of information from the pieces of information constituting the grouping information appended to the specific image signal. In the step S13, a plurality of predetermined pieces of information may be selected from the pieces of information constituting the grouping information appended to the specific image signal. Therefore, in a step S14, all of image signals, which are appended with the same piece of information as the predetermined piece of information having been selected from the pieces of information constituting the grouping information appended to the specific image signal, are read from the storage means 1. In a step S15, processing for reflecting the subsidiary information, which is appended to the specific image signal, upon an image signal is performed by the processing means 6 on all of the image signals having thus been read from the storage means 1.

For example, in the step S13, as the predetermined piece of information among the pieces of information constituting the grouping information appended to the specific image signal, the examination ID number shown in FIG. 4 may be selected. In such cases, in the step S14, all of the image signals appended with the grouping information containing the selected examination ID number are read from the storage means 1. In the step S15, the subsidiary information, which is appended to the specific image signal, such as the grouping information appended to the specific image signal and/or the image processing information giving specifics about image processing having been performed on the specific image signal, is reflected upon all of the image signals having thus been read from the storage means 1. In such cases, all of pieces of information constituting the subsidiary information appended to the specific image signal may be reflected upon the image signals. Alternatively, in cases where the examination ID number shown in FIG. 4 is selected as the predetermined piece of information among the pieces of information constituting the grouping information appended to the specific image signal, as the subsidiary information, only the pieces of information with respect to the examination, the series, and the image shown in FIG. 4 may be reflected upon the image signals.

When the subsidiary information, such as the grouping information, the name of file, and/or the image processing information, is appended to image signals, it may occur that different subsidiary information is appended by mistake to certain image signals, which are among the image signals belonging to the same group. In such cases, it is necessary for operations to be performed for finding out the image signals appended with the incorrect subsidiary information and correcting the subsidiary information appended to the image signals. However, it may occur that incorrect subsidiary information is inputted at the time of the correction or necessary correction is not made perfectly. However, as for the grouping information appended to image signals, if an incorrect piece of information is given by mistake among the pieces of information constituting the grouping information, it will not occur that all of the other pieces of information constituting the grouping information are incorrect. Therefore, with the second embodiment of the image processing apparatus in accordance with the present invention, an image signal appended with correct grouping information is selected as the specific image signal, and the subsidiary information appended to the specific image signal is reflected upon all of the image signals, which are appended with the same piece of information as the predetermined piece of information having been selected from the pieces of information constituting the grouping information appended to the specific image signal. Accordingly, error in correction or imperfect correction do not occur. Also, consistency of the subsidiary information can be obtained easily with respect to the image signals appended with the same grouping information.

What is claimed is:

1. An image processing method, wherein predetermined processing is performed with respect to a plurality of image signals, each of which is appended with grouping information, wherein the image signals appended with identical grouping information represent images associated with one another, the method comprising the steps of:
   in cases where the predetermined processing is performed with respect to a specific image signal, performing the predetermined processing with respect to all of image signals, which are appended with the same grouping information as the grouping information appended to the specific image signal,
   wherein the predetermined processing is a processing for altering subsidiary information appended to the image signal,
   wherein said grouping information comprises information about a patient, an examination, a series number within an identical examination number and an image, and
   wherein said subsidiary information comprises said grouping information, a file name of the image signal, and image processing information.

2. An image processing method according to claim 1, wherein the plurality of image signals represent the same object.

3. An image processing method according to claim 1, wherein said grouping information is appended to an image signal when the image signal is generated.

4. An image processing method according to claim 1, wherein said grouping information about a patient comprises a name of patient, a patient ID number, a sex of the patient, and a date of birth of the patient.

5. An image processing method according to claim 1, wherein said grouping information about an examination comprises an examination ID number, a date of the examination, a time of the examination, and a name of the examination.

6. An image processing method according to claim 1, wherein said grouping information about an image comprises an image ID number and an image recording menu.

7. An image processing method according to claim 1, wherein said image signal is generated by image input modalities comprising at least one of a CR apparatus, a CT scanner, and an MRI apparatus.

8. An image processing apparatus, comprising processing means for performing predetermined processing with respect to a plurality of image signals, each of which is appended with grouping information, wherein the image signals appended with identical grouping information represent images associated with one another,
   wherein the processing means operates such that, in cases where the processing means performs the predetermined processing with respect to a specific image signal, the processing means also performs the predetermined processing with respect to all of image signals, which are appended with the same grouping information as the grouping information appended to the specific image signal,
   wherein the predetermined processing is a processing for altering subsidiary information appended to the image signal,
   wherein said grouping information comprises information about a patient, an examination, a series number within an identical examination number and an image; and
   wherein said subsidiary information comprises said grouping information, a file name of the image signal, and image processing information.

9. A recording medium, on which a program for causing a computer to execute an image processing method has been recorded and from which the computer is capable of reading the program, the image processing method comprising performing predetermined processing with respect to a plurality of image signals, each of which is appended with grouping information, wherein the image signals appended with identical grouping information represent images associated with one another,
   wherein the program comprises the procedures for:
   in cases where the predetermined processing is performed with respect to a specific image signal, performing the predetermined processing with respect to all of image signals, which are appended with the same grouping information as the grouping information appended to the specific image signal,
   wherein the predetermined processing is a processing for altering subsidiary information appended to the image signal,
   wherein said grouping information comprises information about a patient, an examination, a series number within an identical examination number and an image, and
   wherein said subsidiary information comprises said grouping information, a file name of the image signal, and image processing information.

10. An image processing method, wherein predetermined processing is performed with respect to a plurality of image signals, each of which is appended with grouping information, wherein the image signals appended with identical grouping information represent medical images associated with one another, wherein the method comprising the steps of:
   in cases where the predetermined processing is performed with respect to a specific image signal, performing the predetermined processing with respect to all of image signals, which are appended with the same grouping information as the grouping information appended to the specific image signal,
   wherein the predetermined processing is a processing for altering subsidiary information appended to the image signal,
   wherein said grouping information comprises information about a patient, an examination, a series number within an identical examination number and an image, and
   wherein said subsidiary information comprises said grouping information, a file name of the image signal, and image processing information.

* * * * *